United States Patent [19]

Lukach et al.

[11] Patent Number: 4,853,437

[45] Date of Patent: Aug. 1, 1989

[54] WATER- AND CAUSTIC-INSOLUBLE, INSWELLABLE, FIBROUS, PARTICULATE CROSSLINKED POLYMER

[75] Inventors: Carl A. Lukach, Katy, Tex.; Arjun C. Sau, Newark, Del.

[73] Assignee: Hercules Incorporated, Wilmington, Del.

[21] Appl. No.: 164,165

[22] Filed: Mar. 4, 1988

[51] Int. Cl.[4] ............................................. C08L 63/10
[52] U.S. Cl. .................................. 525/54.21; 523/411; 523/412; 523/414; 523/420; 523/446; 523/447; 523/448; 525/54.2; 525/113; 525/201; 525/205; 525/218; 527/312
[58] Field of Search .................... 523/446, 447, 448; 525/54.21, 54.2, 113; 527/312

[56] References Cited

U.S. PATENT DOCUMENTS

| | | | |
|---|---|---|---|
| 3,700,623 | 10/1972 | Keim | 525/328.3 |
| 3,833,531 | 9/1974 | Keim | 525/328.3 |
| 3,941,736 | 3/1976 | Aldrich | 525/416 |
| 4,017,431 | 4/1977 | Aldrich | 523/417 |
| 4,198,269 | 4/1980 | Evari et al. | 524/35 |
| 4,222,921 | 9/1980 | Van Eenar | 525/328.3 |
| 4,273,892 | 8/1981 | Rave | 524/17 |
| 4,537,831 | 8/1985 | Di Stefano | 525/203 |
| 4,604,217 | 8/1986 | Lukach et al. | 252/8.55 |
| 4,735,738 | 4/1988 | Willman | 428/170 |

*Primary Examiner*—John C. Bleutge
*Assistant Examiner*—David W. Woodward
*Attorney, Agent, or Firm*—Mark D. Kuller

[57] ABSTRACT

This invention relates to a novel composition comprising a water- and caustic-insoluble, inswellable, fibrous, particulate polymer comprising cross-linked units of a water-soluble polymer and a water-soluble cationic poly(diallylamine)-epichlorohydrin resin. This polymer is useful as an exchange resin, tablet disintegrant, thickener and suspending aid.

19 Claims, No Drawings

WATER- AND CAUSTIC-INSOLUBLE, INSWELLABLE, FIBROUS, PARTICULATE CROSSLINKED POLYMER

This invention relates to a novel water- and caustic-insoluble, inswellable, fibrous, particulate polymer comprising cross-linked units of a water-soluble polymer and a water-soluble cationic poly(diallylamine)-epichlorohydrin resin. This polymer is useful as an exchange resin, tablet disintegrant and suspending aid.

BACKGROUND OF THE INVENTION

Lukach et al, in U.S. Pat. No. 4,604,217, disclose a gelled aqueous composition comprising fresh water or brine having a pH greater than 10 and (a) a water thickening amount of (i) an anionic water soluble polymer selected from the group consisting of alkali metal salts of carboxymethyl cellulose, carboxymethyl hydroxyethyl cellulose, carboxymethyl guar, carboxymethyl hydroxyethyl guar, carboxymethyl hydroxypropyl guar, xanthan gum and copolymers of sodium acrylate having from about 10% to about 90% acrylate content or (ii) nonionic water soluble polymer selected from the group consisting of polyacrylamides, polyacrylonitrile, polyvinylpyrrolidone, copolymers of acrylamide, hydroxyethyl cellulose, methyl cellulose, methylhydroxyethyl cellulose, ethylhydroxyethyl cellulose, hydroxypropyl hydroxyethyl cellulose, hydroxyethyl guar and hydroxypropyl guar, and (b) a water soluble cationic poly(diallylamine)-epichlorohydrin resin in an amount sufficient to cause a gel to form.

There has been a need for a particulate polymer which is both water- and caustic-insoluble. Applicant has discovered that such a polymer can be prepared by cross-linking anionic and nonionic polymers, such as those discussed by Lukach et al, or cationic polymers containing hydroxyl groups with the aforementioned cationic resin.

SUMMARY OF THE INVENTION

Accordingly, this invention is directed to a novel composition of matter comprising a water- and caustic-insoluble, inswellable, fibrous, particulate polymer comprising cross-lined units of:

(a) (i) a water-soluble anionic polymer selected from the group consisting of alkali metal salts of carboxymethyl cellulose, carboxymethyl hydroxyethyl cellulose, carboxymethyl guar, carboxymethyl hydroxyethyl guar, carboxymethyl hydroxypropyl guar, xanthan gum and copolymers of sodium acrylate having from about 10% to about 90% acrylate content, or (ii) a water-soluble nonionic water soluble polymer selected from the group consisting of polyacrylamides, polyacrylonitrile, polyvinylpyrrolidone, copolymers of acrylamide, methyl cellulose, hydroxyethyl cellulose, hydroxypropyl cellulose, methylhydroxyethyl cellulose, ethylhydroxyethyl cellulose, methylhydroxypropyl cellulose, methylhydroxybutyl cellulose, hydroxypropyl hydroxyethyl cellulose, hydrophobically modified methyl cellulose, hydrophobically modified hydroxyethyl cellulose, hydrophobically modified hydroxypropyl cellulose, guar, hydroxyethyl guar and hydroxypropyl guar, or (iii) a water-soluble cationic water soluble polymer selected from the group consisting of cationic methyl cellulose, cationic hydroxyethyl cellulose, cationic hydroxypropyl cellulose, cationic methylhydroxyethyl cellulose, cationic ethylhydroxyethyl cellulose, cationic methylhydroxypropyl cellulose, cationic methylhydroxybutyl cellulose, cationic hydroxypropyl hydroxyethyl cellulose, hydrophobically modified cationic methyl cellulose, hydrophobically modified cationic hydroxyethyl cellulose, hydrophobically modified cationic hydroxypropyl cellulose, cationic guar, cationic hydroxyethyl guar and cationic hydroxypropyl guar; and (b) a water-soluble cationic poly(diallylamine)-epichlorohydrin resin.

DETAILED DESCRIPTION OF THE INVENTION

Suitable anionic polymers for use in this invention include the alkali metal salts of carboxymethyl cellulose (CMC), carboxymethyl hydroxyethyl cellulose (CMHEC), carboxymethyl guar, carboxymethyl hydroxyethyl guar, carboxymethyl hydroxypropyl guar, xanthan gum and copolymers of sodium acrylate having from about 10% to about 90%, preferably about 10% to about 50%, most preferably 10% to about 30%, acrylate content. The carboxymethyl derivatives typically have a carboxymethyl (C.M.) degree of substitution (D.S.) (the average number of substituted hydroxyl groups per anhydroglucose unit of the cellulose molecule or per anhydrohexose unit of the guar molecule) of about 0.1 to 1.5, preferably from about 0.1 to 1.0, except CMC which preferably has a C.M.D.S. of 0.7 to 0.9. The hydroxyethyl or hydroxypropyl molar substitution (MS) (the average number of moles of ethylene oxide or propylene oxide substituted hydroxyl groups per anhydroglucose unit of the cellulose molecule or per anhydrohexose unit of the guar molecule) of these polymers is generally from about 0.15 to about 3.0, preferably from about 1.0 to about 2.5, most preferably from 1.5 to 2.5. Suitable alkali metals include sodium and potassium. Sodium is the preferred alkali metal. These polymers and their preparation as well known in the art and are described in, for example, Handbook of Water-Soluble Gums and Resins (Robert L. Davidson, Ed. 1980), Industrial Gums (Roy L. Whistler, Ed., Second Ed., 1973) and R. L. Whistler and C. L. Smart, Polysaccharide Chemistry (1953).

Xanthan gum is a high-molecular weight carbohydrate. It is a polysaccharide produced by fermentation by the Xanthomonas microorganism, usually Xanthomonas campestris.

Suitable copolymers of sodium acrylate include sodium acrylate-acrylamide copolymers and sodium acrylate-methacrylamide copolymers. The sodium acrylate-acrylamide copolymer is preferred. Typically the molecular weight of such copolymers ranges from about 50,000 to about 30,000,000. The preparation of copolymers of sodium acrylate is well known in the art.

The preferred anionic polymers for use in this invention are CMC and CMHEC.

Nonionic water soluble polymers useful in this invention include polyacrylamides, polyacrylonitrile, polyvinylpyrrolidone, copolymers of acrylamide, methyl cellulose, hydroxyethyl cellulose (HEC), hydroxypropyl cellulose, methylhydroxyethyl cellulose, ethylhydroxyethyl cellulose, methylhydroxypropyl cellulose, methyl hydroxybutyl cellulose, hydroxypropyl hydroxyethyl cellulose, hydrophobically modified methyl cellulose, hydrophobically modified hydroxyethyl cellulose, hydrophobically modified hydroxypropyl cellulose, hydroxyethyl guar and hydroxypropyl guar. HEC is preferred.

Polyacrylamides, polyacrylonitrile, polyvinylpyrrolidone and copolymers of acrylamide are well known in the art and are commercially available. Generally, these polymers have a molecular weight of from about 50,000 to about 30,000,000. Polyacrylamide and polyvinylpyrrolidone are described in the Handbook of Water-Soluble Gums, and Resins, cited above.

The nonionic cellulose and guar derivatives are also well known in the art. Typically, the hydroxyethyl or hydroxypropyl M.S. of the cellulose and guar ethers is from about 0.15 to about 3.0, preferably 0.2 to about 2.5. The methyl and ethyl D.S. of these ethers generally ranges from about 0.1 to about 1.0. The cellulosic derivatives and their preparation are described in Handbook of Water-Soluble Gums and Resins, Industrial Gums and Polysaccharide Chemistry, all cited above.

The preferred hydrophobically modified methyl hydroxyethyl, and hydroxypropyl celluloses, are hydrophobically modified with a long chain alkyl group in an amount between about 0.2 weight percent and the amount which renders said cellulose ether less than 1 weight percent soluble in water as described by Landoll, in U.S. Pat. Nos. 4,228,277 and 916. Preferred is water-soluble hydroxyethyl cellulose (substrate having a molecular weight of about 50,000 to 400,000) substituted with a long chain alkyl radical having 6 to 18 carbon atoms, having a hydroxyethyl M.S. of 1.5 to 3.5.

Suitable water-soluble cationic polymers are those which contain hydroxyl groups, e.g., cationic methyl cellulose, cationic hydroxyethyl cellulose, cationic hydroxypropyl cellulose, cationic methylhydroxyethyl cellulose, cationic ethylhydroxyethyl cellulose, cationic methylhydroxypropyl cellulose, cationic methylhydroxybutyl cellulose, cationic hydroxypropyl hydroxyethyl cellulose, hydrophobically modified cationic methyl cellulose, hydrophobically modified cationic hydroxyethyl cellulose, hydrophobically modified cationic hydroxypropyl cellulose, cationic guar, cationic hydroxyethyl guar and cationic hydroxypropyl guar. Preferred are cationic derivatives of hydroxyethyl cellulose, guar and hydrophobically modified hydroxyethyl cellulose. Cationic modifier are well known in the art. A typical cationic derivative is hydroxyethyl cellulose modified with glycidal trialkyl ammonium halide.

Water soluble cationic poly(diallylamine)-epihalohydrin resins useful in this invention are formed by the reaction of poly(diallylamine) with an epihalohydrin. They are described by Lukach et al in U.S. Pat. No. 4,604,217, cited above. They typically have a molecular weight of from 100 to 20,000,000, preferably 50,000 to 10,000,000, most preferably 50,000 to 3,000,000. The activated form of these resins, which are at a pH of at least 8, are believed to be almost completely comprised of repeating units of the formula:

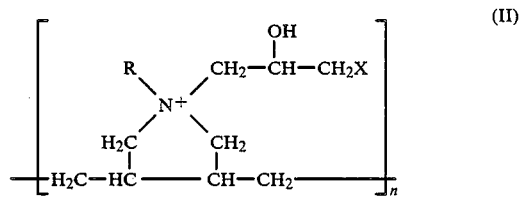

(I)

wherein R is $C_{1-4}$ alkyl, X is a halide anion and n is an integer sufficient to provide a resin having a molecular weight from about 100 to about 20,000,000. There can also be some short chain branching in the repeat polymer units as a result of the ability of the epoxide group to chain out.

Examples of R include methyl, ethyl, propyl, isopropyl and butyl. Methyl is preferred. Generally the halide anion is chloride or bromide. The preferred water soluble cationic resin for use in this invention is poly(N-methyldiallylamine)-epichlorohydrin.

At acidic pH, i.e. a pH of less than 5, the resins are believed to be almost completely comprised of repeating units of the formula:

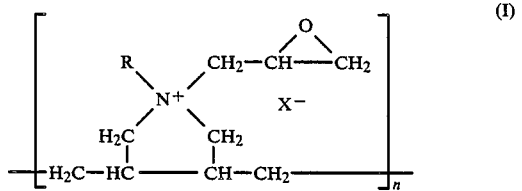

(II)

where R, X and n are as set forth above.

The resins are prepared by polymerizing the hydrohalide salt of a diallylamine and reacting poly(diallylamine) thus formed with an epihalohydrin, particularly epichlorohydrin, by the method of preparation known in the art. See, for example, the methods disclosed by Keim in U.S. Pat. Nos. 3,700,623 and 3,833,531 respectively. The resulting solution of resin prior to dilution generally has a total solids content of about 20% to about 21%.

Poly(diallylamine)-epihalohydrin resins are prepared in aqueous solution at a pH of from about 7 to about 9.5 and the resins will contain units of the structure I above and have a tendency to gel on standing. The resin solution is stabilized against gelation by adding to the aqueous solution thereof sufficient acid, such as hydrochloric acid, to obtain and maintain the pH at about 2 and the resin will contain units of the structure II. They are usually marketed in this acid-stabilized form. The acid-stabilized resins are reactivated prior to use by known means to reestablish the I structure. Such acid-stabilized resin solutions and means of reactivating same are disclosed in U.S. Pat. No. 3,833,531, cited above. The preferred means of reactivation is by addition of aqueous NaOH.

The ratio of the polymers (a) to resins (b) of this invention is in the range of 100:5 to 100:20, by weight, and preferably is about 100:10.

By "caustic-insoluble" it is meant that the polymer of this invention is less than 1 weight percent soluble in a 10 weight percent sodium hydroxide solution. Caustic insolubility is readily determined by a simple test. Specifically, five grams of polymer is added to two hundred grams of a 10% sodium hydroxide solution at room temperature and the resultant slurry is vigorously agitated for one half hour. Then, the slurry is filtered and the residue is washed thoroughly with water until it is caustic free, dried in an oven at 80° C. for two hours, and weighed. If greater than 99 weight percent of the polymer is recovered the polymer is "caustic-insoluble" as defined above.

The cross-linked polymers of this invention are flowable, discreet, fibrous and particulate. They are not water-soluble, i.e., are less than about 0.1%, by weight, soluble in water. They are "inswellable", i.e., are not hydrophilic in nature and do not swell with water so as to form gels.

The polymers of this invention have a greater degree of cross-linking than those described by Lukach et al. Further, they are generally formed in organic media, whereas the polymers of Lukach et al are formed in an aqueous solution in a well.

The cross-linked polymers of this invention can be prepared by reacting the water-soluble polymer (a) with the water-soluble cationic poly(diallylamine)-epichlorohydrin resin (b) under alkaline conditions at elevated temperatures, e.g., 80° C. or higher. It can also be prepared by a single-step process whereby alkali cellulose is simultaneously reacted with monochloroacetic acid, ethylene oxide and poly(diallylamine)-epichlorohydrin at elevated temperatures.

The polymers of this invention and their preparation are illustrated in the following examples, which are exemplary and not intended to be limiting. Therein, and throughout this specification, all percentages, parts, etc., are by weight unless otherwise indicated.

EXAMPLE 1

This example shows an embodiment of the polymer of this invention and how to prepare it.

Extrainer PHV wood pulp (wood pulp comprised of approximately 90% alpha-cellulose and a remainder of mainly hemicellulose having an intrinsic viscosity measured in cupraethylenediamine (cuene) solution of 10.7 liters/g, made from soft wood, available from Rayonier Inc., Stamford, Connecticut) (84g "as is" weight) was added to a mixture of t-butyl alcohol (630g) and caustic solution (26.8g of NaOH dissolved in 120g of water) in a Stainless Steel reactor. The resulting cellulose slurry was vigorously agitated at 20° C. for 30 minutes in a nitrogen atmosphere. Ethylene oxide was added to the slurry and it was heated at 80° C. for 30 minutes to bring about hydroxyethylation. The contents of the reactor were cooled to 55° C. and, then, a solution of monochloroacetic acid (25g) in t-butyl alcohol (55g) and water (5.6g) was added to the reactor. The resulting reaction mixture was heated at 70° C. for 30 minutes to bring about the carboxymethylation. The resultant CMHEC had a carboxymethyl D.S. of 0.4 and a hydroxyethyl M.S. of 0.9. While maintaining the temperature at 70° C., a 50% sodium hydroxide solution (5g) and 20% poly(N-methyldiallylamine)-epichlorohydrin resin (45g) were added. The resulting mixture was heated at 90° C. for 1 hour to bring about cross-linking. Afterwards, the reaction mixture was filtered, the residue was washed 3 times with water at room temperature to remove salts and by-products, the washed product was dehydrated with acetone, and the dehydrated product was dried in a fluid bed dryer at 50° C. to yield 116g of a particulate product, which was less than 1 weight % soluble in a 10 weight % NaOH solution, and contained as impurities 5% moisture and 10.7% ash ($Na_2SO_4$).

EXAMPLE 2

This example shows an embodiment of the polymer of this invention and preparation of the polymer by way of a single step process.

Extrainer PHV wood pulp (84g "as is" weight) was added to a mixture of t-butyl alcohol (630g) and caustic solution (26.8g of NaOH dissolved in 120g of water) in a Stainless Steel reactor. The resulting cellulose slurry was vigorously agitated at 20° C. for 30 minutes in a nitrogen atmosphere. To this alkalized cellulose slurry were added to the following:

(a) fifty (50) grams of a 20% poly(N-methyldiallylamine)-epichlorohydrin resin;
(b) a solution comprising 14 grams of monochloroacetic acid in 50 grams of t-butyl alcohol and 20 grams of water; and
(c) sixty (60) grams of ethylene oxide.

The resulting mixture was heated at 80° C. for 1 hour and then cooled to room temperature. Afterwards, the reaction mixture was filtered, the residue was washed 3 times with water at room temperature to remove salts and by-products, the washed product was dehydrated with acetone, and the dehydrated product was dried in a fluid bed dryer at 50° C. to yield 116g of a particulate product, which was less than 1 weight percent soluble in a 10 weight percent sodium hydroxide solution.

EXAMPLE 3

This example shows an embodiment of the polymer of this invention and how to prepare it.

Extrainer PHV wood pulp (84g "as is" weight), t-butyl alcohol (630g), NaOH pellets (26.8g) and water (120g) were mixed in a Stainless Steel reactor at 20° C. for 30 minutes in a nitrogen atmosphere to form an alkalized cellulose slurry. Ethylene oxide was added to the slurry and it was heated at 80° C. for 1 hour to bring about hydroxyethylation (The resultant HEC had a hydroxyethyl M.S. of 2.8). Then, after cooling the reaction mixture to 55° C., 70% nitric acid (42g) solution was added, followed by the addition of 20% poly(N-methyldiallylamine)-epichlorohydrin resin (50g). The resulting reaction mixture was heated at 90° C. for 90 minutes and cooled to room temperature. A wet cake was obtained by filtration of the reaction mixture, followed by washing the residue three times with water. The wet cake was hardened with acetone and dried in a fluid bed dryer at 60° C. for 1 hour. The resultant produce was a particulate polymer, which was less than 1 weight percent soluble in a 10 weight percent NaOH solution, and has as impurities 3.9% moisture and 0.25% ash ($Na_2SO_4$).

The polymer of this invention provides good disintegration characteristics and dissolution rates. Therefore, it can be used as a disintegrant in, e.g., drug tablets. It is also useful as a suspending aid for lotions and dispersions of, e.g., drugs, pigments, etc.

The polymer of this invention can be used to absorb oils and surfactants, for instance, in removing ionic surfactants, together with bound oils and greases, from industrial waste streams. In addition, it can be used as an exchange resin to selectively remove metallic ions in, for example, water treatment and testing.

While the invention has been described with respect to specific embodiments, it should be understood that they are not intended to be limiting and that many variations and modifications are possible without departing from the scope of this invention.

I claim:

1. A composition of matter comprising a water- and caustic-insoluble, inswellable (does not swell with water so as to form gels), fibrous, particulate polymer comprising:

(a) units of (i) a water-soluble anionic polymer selected from the group consisting of alkali metal salts of carboxymethyl cellulose, carboxymethyl hydroxyethyl cellulose, carboxymethyl guar, carboxymethyl hydroxyethyl guar and carboxymethyl hydroxypropyl guar, xanthan gum, and copolymers of sodium acrylate having from about 10% to about 90% acrylate content, or (ii) a nonionic, water-soluble polymer selected from the group consisting of polyacrylamides, polyacrylonitrile, polyvinylpyrrolidone, copolymers of acrylamide, methyl cellulose, hydroxyethyl cellulose, hydroxypropyl cellulose, methylhydroxyethyl cellulose, ethylhydroxyethyl cellulose, methylhydroxypropyl cellulose, methylhydroxybutyl cellulose, hydroxypropyl hydroxyethyl cellulose, hydrophobically modified methyl cellulose, hydrophobically modified hydroxyethyl cellulose, hydrophobically modified hydroxypropyl cellulose, guar, hydroxyethyl guar and hydroxypropyl guar, or (iii) a water-soluble cationic water soluble polymer selected from the group consisting of cationic methyl cellulose, cationic hydroxyethyl cellulose, cationic hydroxypropyl cellulose, cationic methylhydroxyethyl cellulose, cationic ethylhydroxyethyl cellulose, cationic methylhydroxypropyl cellulose, cationic methylhydroxybutyl cellulose, cationic ethylhydroxyethyl cellulose, cationic hydroxypropyl hydroxyethyl cellulose, hydrophobically modified cationic methyl cellulose, hydrophobically modified cationic hydroxyethyl cellulose, hydrophobically modified cationic hyroxypropyl cellulose, cationic guar, cationic hydroxyethyl guar and cationic hydroxypropyl guar; cross-linked with (b) units of a water-soluble cationic poly(diallylamine)-epichlorohydrin resin.

2. A composition of matter as claimed in claim 1 wherein the water-soluble polymer (a) is the anionic polymer.

3. A composition of matter as claimed in claim 2 wherein the anionic polymer is the alkali metal salt of carboxymethyl cellulose.

4. A composition of matter as claimed in claim 3 wherein the alkali metal salt of carboxymethyl cellulose water is a sodium salt of carboxymethyl cellulose having a carboxymethyl degree of substitution of 0.7 to 0.9.

5. A composition of matter as claimed in claim 2 wherein the anionic polymer is the carboxymethyl hydroxyethyl cellulose.

6. A composition of matter as claimed in claim 5 wherein the carboxymethyl hydroxyethyl cellulose is a sodium salt of carboxymethyl hydroxyethyl cellulose having a carboxymethyl degree of substitution of about 0.1 to 1.5 and a hydroxyethyl molar substitution of from about 0.15 to about 3.0.

7. A composition of matter as claimed in claim 1 wherein the water-soluble polymer (a) is the nonionic water soluble polymer.

8. A composition of matter as claimed in claim 7 wherein the nonionic polymer is the hydroxyethyl cellulose.

9. A composition of matter as claimed in claim 8 wherein the hydroxyethyl cellulose has a hydroxyethyl molar substitution of from about 0.15 to about 3.0.

10. A composition of matter as claimed in claim 7 wherein the water-soluble polymer (a) is the hydrophobically modified hydroxyethyl cellulose.

11. A composition of matter as claimed in claim 7 wherein the hydrophobically modified hydroxyethyl cellulose is prepared from a water-soluble hydroxyethyl cellulose substrate having a molecular weight of about 50,000 to 400,000, substituted with a long chain alkyl radical having 6 to 18 carbon atoms, having a hydroxyethyl M.S. of 1.5 to 3.5.

12. A composition of matter as claimed in claim 1 wherein the water-soluble polymer (a) is the cationic polymer.

13. A composition of matter as claimed in claim 12 wherein the cationic polymer is cationic hydroxyethyl cellulose.

14. A composition of matter as claimed in claim 12 wherein the cationic polymer is hydrophobically modified cationic hydroxyethyl cellulose.

15. A composition of matter as claimed in claim 12 wherein the cationic polymer is cationic guar.

16. A composition of matter as claimed in claim 2 wherein the ratio (a):(b) is in the range of 100:5 to 100:20, by weight.

17. A composition of matter as claimed in claim 7 wherein the ratio (a):(b) is in the range of 100:5 to 00:20, by weight.

18. A composition of matter as claimed in claim 12 wherein the ratio (a):(b) is in the range of 100:5 to 100:20, by weight.

19. A composition of matter as claimed in claim 1 wherein the ratio (a):(b) is about 100:10.

* * * * *

UNITED STATES PATENT AND TRADEMARK OFFICE
CERTIFICATE OF CORRECTION

PATENT NO. : 4,853,437

DATED : AUGUST 1, 1989

INVENTOR(S) : LUKACH & SAU

It is certified that error appears in the above-identified patent and that said Letters Patent is hereby corrected as shown below:

Column 1, Line 45

"cross-lined" should read --cross-linked--

Column 2, Line 38

"as well known" should read --are well known--

Column 3, Line 42

"modifier" should read --modifiers--

Column 4, Line 25

"method" should read --methods--

UNITED STATES PATENT AND TRADEMARK OFFICE
CERTIFICATE OF CORRECTION

PATENT NO. : 4,853,437

DATED : AUGUST 1, 1989

INVENTOR(S) : LUKACH & SAU

It is certified that error appears in the above-identified patent and that said Letters Patent is hereby corrected as shown below:

Column 5, Line 68

"were added to" should read --were added--

Column 6, Line 36

"produce" should read --product--

Column 7, Claim 1, Line 25

"hyroxypropyl" should read --hydroxypropyl--

Column 8, Claim 17, Line 38

"100:5 to 00:20," should read --100:5 to 100:20,--.

Signed and Sealed this

Tenth Day of July, 1990

*Attest:*

HARRY F. MANBECK, JR.

*Attesting Officer*   *Commissioner of Patents and Trademarks*